United States Patent
Geistert et al.

Patent Number: 6,053,868
Date of Patent: Apr. 25, 2000

[54] APPARATUS FOR A CARDIOLOGICAL THERAPY

[75] Inventors: Wolfgang Geistert, Rheinfelden-Herten; Achim Kitschmann, Grenzach-Wyhlen, both of Germany

[73] Assignee: Sulzer Osypka GmbH, Grenzach-Wyhlen, Germany

[21] Appl. No.: 09/060,933

[22] Filed: Apr. 15, 1998

[30] Foreign Application Priority Data

Apr. 24, 1997 [EP] European Pat. Off. .............. 97810252

[51] Int. Cl.[7] ................................ A61B 8/00; A61B 8/12
[52] U.S. Cl. .................... 600/439; 600/450; 600/471; 607/122
[58] Field of Search ...................... 600/439, 450, 600/456; 601/2; 606/1; 607/122

[56] References Cited

U.S. PATENT DOCUMENTS

| | | |
|---|---|---|
| 3,938,502 | 2/1976 | Bom . |
| 5,385,148 | 1/1995 | Lesh . |
| 5,544,656 | 8/1996 | Pitsillides et al. ................ 600/450 |
| 5,588,432 | 12/1996 | Crowley . |
| 5,657,760 | 8/1997 | Ying et al. ........................ 600/439 |
| 5,803,083 | 9/1998 | Buch et al. ....................... 600/439 |
| 5,893,848 | 4/1999 | Negus et al. ..................... 607/122 |

*Primary Examiner*—Francis J. Jaworski
*Attorney, Agent, or Firm*—Townsend and Townsend and Crew LLP

[57] ABSTRACT

The apparatus for a cardiological therapy, in particular an ablation apparatus, comprises an ultrasonic transducer and an applicator which is arranged at the transducer and provided for an endocardial energy output. An echocardiographic thickness measurement of the myocardium can be performed by means of the transducer. Control means are provided by means of which the energy output is metered with the applicator and can be performed in a manner matched to the measured thickness.

17 Claims, 1 Drawing Sheet

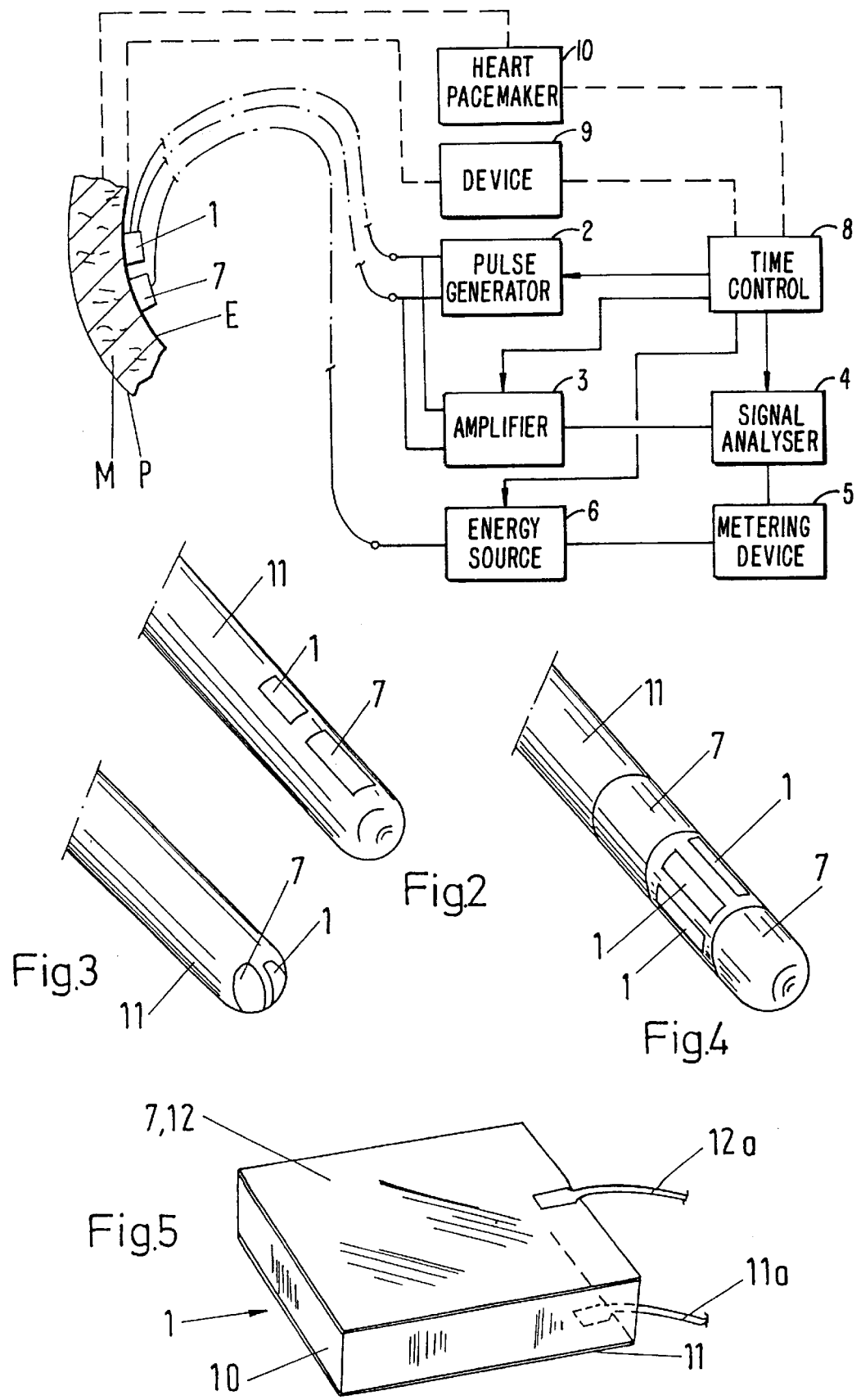

APPARATUS FOR A CARDIOLOGICAL THERAPY

BACKGROUND OF THE INVENTION

1. Field of the Invention

The invention relates to an apparatus for a cardiological therapy, in particular to an ablation apparatus, consisting of an ultrasonic transducer and an applicator adjacent to the transducer for providing an endocardial energy output.

2. Description of the Prior Art

Ablation apparatuses serve to eliminate disturbances in the heart rhythm by means of electrocardial operations. With known apparatuses the heart tissue is heated locally to such an extent that only the electrical properties of the tissue are damaged. A high frequency generator (e.g. Osypka HAT200S, HAT300, Medtronic Atakr, EPT 1000) is often used as an energy source for the ablation. Ultrasound and microwaves can also used as energy sources. Furthermore, an ablation can also be performed by undercooling or by means of chemical substances. These two intervention possibilities are also included here in connection with the term "energy output".

The energy output is advantageously regulated by means of a temperature measurement performed at the applicator. This regulation serves to prevent a coagulation of the tissue as well as of the blood and thus the formation of thromboses.

WO 95/17131 describes a catheter and a method in which the position of the catheter relative to the tissue can be determined by means of ultrasound. The goal is to give off the energy only when the catheter is in a suitable orientation relative to the tissue and is in direct contact with it. The energy can thus be introduced into the tissue with a good efficiency; an unnecessary and damaging output of energy to the blood is therein avoided.

As is known, the thickness of the myocardium can be measured echocardiographically by means of ultrasound (see e.g. J. H. Myers et al. "Direct Measurement of Inner and Outer Wall Thickening Dynamics with Epicardial Echocardiography", Circulation, Vol. 74, No. 1, Jul. 1986, pages 164 ff.). Tissue dimensions, and in particular myocardium thicknesses, can be determined using most of the picture producing ultrasound devices.

In the case of frequent disturbances in the heart rhythm, such as for instance auricular fibrillation, it is important that the electrical properties of the myocardium are thoroughly destroyed in depth so that no further excitation conduction can take place in the treated tissue. The elimination of fibrillation in particular, which results in chaotic excitations, means that it is in many cases difficult to assess the success of the ablation in an electrical manner.

SUMMARY OF THE INVENTION

The object of the invention is thus to provide an apparatus for a cardiological therapy, in particular an ablation apparatus, in which the tissue to be treated is, in fact, thoroughly denatured after the energy emission with a high degree of reliability. In this process, only the electrical properties of the tissue are to be altered, and indeed to just such an extent that disturbances in the heart rhythm no longer occur afterwards.

This object is satisfied by the apparatus present invention. A metering of the energy output is possible with this apparatus. The thickness of the myocardium is determined by means of ultrasound; the output of the therapeutic energy can be regulated on the basis of the measured thickness. The energy can be intentionally metered using the apparatus in accordance with the invention in such a manner that throughgoing denaturing of the tissue results without layers which lie at a greater distance from the applicator being irreparably damaged at the same time.

The apparatus in accordance with the invention for a cardiological therapy, in particular an ablation apparatus, comprises an ultrasonic transducer and an applicator which is arranged at the transducer and provided for an endocardial energy output. An echocardiographic thickness measurement of the myocardium can be performed by means of the transducer. Control means are provided by means of which the energy output is metered with the applicator and can be performed in a manner matched to the measured thickness.

BRIEF DESCRIPTION OF THE DRAWINGS

FIG. 1 is a block circuit diagram of the apparatus in accordance with the invention, FIG. 2 is the distal end of a catheter for the apparatus in accordance with the invention, FIG. 3 is the distal end of a catheter in accordance with a second embodiment, FIG. 4 is a third embodiment and FIG. 5 is an element in which the ultrasonic transducer and the applicator form a unit.

DETAILED DESCRIPTION OF THE PREFERRED EXEMPLARY EMBODIMENTS

The following components are comprised by the apparatus in accordance with the block diagram of FIG. 1: an ultrasonic transducer 1, a pulse generator 2, an amplifier 3, a signal analyser 4, a metering device 5, an energy source 6, an applicator 7 and a time control 8. Furthermore the apparatus comprises—in special embodiments only—a device 9 which perceives the expansion and contraction of the heart and/or a heart pacemaker 10. The transducer 1 and the applicator 7 are arranged at the myocardium M.

An electrical pulse generated in the pulse generator 2 is conducted to the transducer 1, converted there into sonic energy and emitted. Afterwards, the transducer 1 acts as a receiver: it receives the sound waves reflected by the tissue structures and converts them to electrical energy. After passing through the amplifier 3 and after a demodulation provided where appropriate, this energy is conveyed to the signal analyzer 4. There, the reflections which stem from the endocardium E and the pericardium P are determined from an amplitude modulation of the envelope curves. The thickness of the myocardium M can be determined from the time points at which the reflections arrive at the transducer and from the known speed of sound in the tissue.

The value of the thickness of the myocardium determined in this manner is supplied to the metering device 5. The therapeutic energy by means of which the electrical properties of the tissue can be destroyed are determined by means of a computational algorithm related to the energy source or by means of an empirically established database. The metering device 5 transmits the information on the required energy to the energy source 6, which subsequently gives off a corresponding amount of energy via the applicator 7 to the myocardium M, either automatically or upon each request.

The time control 8 coordinates the correct temporal sequence of the process, which is advantageously matched to the movement of the heart.

In preferred embodiments of the invention, the ultrasonic transducer 1 and the applicator 7 are arranged in the same catheter 11: see FIGS. 2 to 4.

It is advantageous if the ultrasonic transducer 1 and the applicator 7 are oriented in such a manner that the energy is given off only in the direction in which the thickness has been measured.

Furthermore, it is advantageous to provide the device 9 shown in FIG. 1 which perceives the expansion and contraction of the heart. In this way, the time point of the thickness measurement can be synchronized with a signal coming from the heart. Thus, the same reproducible relationships are always present during the measurement.

The synchronisation can be considerably facilitated if the heart is periodically stimulated by a heart pacemaker 10 (FIG. 1) and a constant periodicity of the heart movement is thus enforced. The time point of the thickness measurement can also be controlled by the signal of the heart pacemaker 10.

In the exemplary embodiment of FIG. 2 the transducer 1 and the applicator 7 are arranged laterally at the distal end of the catheter 11. In the second exemplary embodiment of FIG. 3, the transducer 1 and the applicator 7 are arranged at the distal tip of the catheter 11. The third exemplary embodiment, of FIG. 4 shows a catheter 11 with two applicators 7 and a plurality of ultrasonic transducers 1.

In a particularly advantageous embodiment of the invention, the transducer 1 and the applicator 7 are integrated in a common element. In FIG 5 an ultrasonic transducer 1 comprises, for example, a platelet-like piezo-crystal 10, each side of which bears an electrode 11, 12. This transducer is arranged in a catheter (not shown) in such a manner that the one electrode 12 is located directly at the surface of the catheter. This electrode 12 can be designed in such a manner that it can be used as an applicator 7. A wire 11a produces an electrical connection to the electrode 11. A second electrical connection 12a forms the connection to the electrode 12 or to the applicator 7. The energy provided for the cardiological therapy is additionally transmitted via the connection 12a.

What is claimed is:

1. An apparatus for a cardiological therapy, the apparatus comprising:
    an ultrasonic transducer for endocardial energy output and for measuring an echocardiographic thickness of a myocardium;
    an applicator arranged adjacent the transducer for endocardial energy output;
    control means for metering the energy output with the applicator in a manner based upon the measured echocardiographic thickness; and
    a device for registering the expansion and contraction of the heart for synchronizing a time point of measurement with the periodicity of heart movement.

2. An apparatus in accordance with claim 1 further comprising a system for endocardial energy output, in addition to the transducer and the applicator, the system comprising:
    a pulse generator;
    an amplifier;
    a signal analyzer;
    an energy source;
    a metering device; and
    a time control;
    wherein the pulse generator is coupled to the transducer for transmitting electrical pulses; and
    wherein the transducer is coupled to the amplifier for transmitting signals produced in the transducer by reflected sound waves.

3. An apparatus in accordance with claim 1 wherein a heart pacemaker is connected to the apparatus while enforcing a constant periodicity of the heart movement as a result of a periodic stimulation, with a time point of the thickness measurement being controllable by a signal of the heart pacemaker.

4. An apparatus in accordance with claim 1 wherein the ultrasonic transducer and the applicator are arranged adjacently in a distal region of a catheter.

5. An apparatus in accordance with claim 4 wherein the transducer and the applicator are oriented in such a manner that an output direction for energy agrees with a direction from which the transducer receives echo signals for the thickness measurement.

6. An apparatus in accordance with claim 4 wherein the ultrasonic transducer and the applicator are integrated in a common element.

7. An apparatus in accordance with claim 4 wherein the transducer and the applicator are arranged laterally on the catheter.

8. An apparatus in accordance with claim 4 wherein the transducer and the applicator are arranged at a distal tip of the catheter.

9. An apparatus in accordance with claim 4 wherein at least one of a plurality of ultrasonic transducers and a plurality of applicators are provided in a distal region of the catheter.

10. An apparatus for a cardiological therapy, the apparatus comprising:
    an ultrasonic transducer for endocardial energy output and for measuring an echocardiographic thickness of a myocardium;
    an applicator arranged at the transducer for endocardial energy output;
    control means for metering the energy output with the applicator in a manner based upon the measured echocardiographic thickness; and
    wherein a heart pacemaker is connected to the apparatus while enforcing a constant periodicity of the heart movement as a result of a periodic stimulation, with a time point of the thickness measurement being controllable by a signal of the heart pacemaker.

11. An apparatus in accordance with claim 10 wherein the ultrasonic transducer and the applicator are arranged adjacently in a distal region of a catheter.

12. An apparatus in accordance with claim 11 wherein the transducer and the applicator are oriented in such a manner that an output direction for energy agrees with a direction from which the transducer receives echo signals for the thickness measurement.

13. An apparatus in accordance with claim 11 wherein the ultrasonic transducer and the applicator are integrated in a common element.

14. An apparatus in accordance with claim 11 wherein the transducer and the applicator are arranged laterally on the catheter.

15. An apparatus in accordance with claim 11 wherein the transducer and the applicator are arranged at a distal tip of the catheter.

16. An apparatus in accordance with claim 11 wherein at least one of a plurality of ultrasonic transducers and a plurality of applicators are provided in a distal region of the catheter.

17. An apparatus in accordance with claim 16 further comprising a system for endocardial energy output, in addition to the transducer and the applicator, the system comprising:

a pulse generator;
an amplifier;
a signal analyzer;
an energy source;
a metering device; and
a time control;

wherein the pulse generator is coupled to the transducer for transmitting electrical pulses; and wherein the transducer is coupled to the amplifier for transmitting signals produced in the transducer by reflected sound waves.

* * * * *